(12) United States Patent
Mao

(10) Patent No.: US 10,501,395 B2
(45) Date of Patent: Dec. 10, 2019

(54) MULTIFUNCTIONAL SYNERGISTIC MACROMOLECULAR ANTI-OXIDATION STABILIZER AND PREPARATION METHOD AND USE THEREOF

(71) Applicant: SHAOXING RUIKANG BIOTECHNOLOGES CO., INC, Paojiang, Shaoxing, Zhejiang (CN)

(72) Inventor: Lijuan Mao, Ontario (CA)

( * ) Notice: Subject to any disclaimer, the term of this patent is extended or adjusted under 35 U.S.C. 154(b) by 0 days.

(21) Appl. No.: 15/535,413

(22) PCT Filed: Dec. 9, 2015

(86) PCT No.: PCT/CN2015/096773
§ 371 (c)(1),
(2) Date: Jun. 13, 2017

(87) PCT Pub. No.: WO2016/095735
PCT Pub. Date: Jun. 23, 2016

(65) Prior Publication Data
US 2017/0334821 A1     Nov. 23, 2017

(30) Foreign Application Priority Data
Dec. 15, 2014 (CN) .......................... 2014 1 0777531

(51) Int. Cl.
| | | |
|---|---|---|
| *C07C 43/178* | (2006.01) | |
| *C07C 323/41* | (2006.01) | |
| *C07C 319/12* | (2006.01) | |
| *C07C 215/50* | (2006.01) | |
| *C07C 213/02* | (2006.01) | |
| *C07C 41/16* | (2006.01) | |
| *C08K 5/3492* | (2006.01) | |
| *C08K 5/3435* | (2006.01) | |
| *C08K 5/13* | (2006.01) | |
| *C07D 211/58* | (2006.01) | |
| *C07D 251/54* | (2006.01) | |
| *C07D 401/14* | (2006.01) | |
| *C08K 5/372* | (2006.01) | |

(52) U.S. Cl.
CPC .......... *C07C 43/1785* (2013.01); *C07C 41/16* (2013.01); *C07C 213/02* (2013.01); *C07C 215/50* (2013.01); *C07C 319/12* (2013.01); *C07C 323/41* (2013.01); *C07D 211/58* (2013.01); *C07D 251/54* (2013.01); *C07D 401/14* (2013.01); *C08K 5/13* (2013.01); *C08K 5/3435* (2013.01); *C08K 5/34922* (2013.01); *C08K 5/34926* (2013.01); *C08K 5/3725* (2013.01)

(58) Field of Classification Search
CPC ... C07C 43/1785; C07C 41/16; C07C 323/41; C07C 319/12; C07C 215/50; C07C 213/02; C08K 5/3725; C08K 5/34926; C08K 5/34922; C08K 5/3435; C07D 401/14; C07D 211/58; C07D 251/54
See application file for complete search history.

(56) References Cited

U.S. PATENT DOCUMENTS 3,338,833 A * 8/1967 Spivack .................. C08K 5/20
252/402

* cited by examiner

*Primary Examiner* — Robert D Harlan
(74) *Attorney, Agent, or Firm* — Erson IP (Nelson IP)

(57) ABSTRACT

Disclosed is an anti-oxidation stabilizer, which has the following structure (A), wherein RI is a connection chain, and the connection chain is a fatty chain, an aromatic structural chain or a fatty and aromatic structurally combined chain; R2 is (B), and X is O, S, N or NH or —CONR—, Z is O, S, N or NH, and X is different from Z; R is a fatty chain, an aromatic group, a sterically hindered amine or sterically hindered phenol, R3 is a fatty chain, an aromatic group, a sterically hindered amine or sterically hindered phenol, and R is identical to R3, or R is different from R3; n is a positive integer including 1, n1 is a positive integer including 1, and n is identical to n1, or n is different from n1.

9 Claims, No Drawings

MULTIFUNCTIONAL SYNERGISTIC MACROMOLECULAR ANTI-OXIDATION STABILIZER AND PREPARATION METHOD AND USE THEREOF

FIELD OF THE INVENTION

The present invention relates to a multifunctional synergistic macromolecular anti-oxidation stabilizer, preparation method thereof and use thereof, which is a novel material antioxidant stabilizing additive that can be directly applied to macromolecular material as an antioxidant stabilizing additive for preservation, color retention, maintenance and the like, and used in products such as plastics, rubbers, fibers, coatings and petroleum, etc.

BACKGROUND OF THE INVENTION

The worldwide sales market of antioxidant stabilization additives is huge. A single type of plastic antioxidants has a global consumption of about 420,000 tons in 2011. Asia-Pacific is currently the region of largest consumption, followed by Europe and North America. It is expected that the sales of materials for antioxidant stabilizer products in 2016 Asia-Pacific will reach 4.8 billion US dollars.

Demands and productions of materials for antioxidant stabilization additives gradually transfer from the United States, Western Europe and Japan to Asia's emerging markets, especially in China and India. At present, the consumption of antioxidants in China is growing rapidly. However, a small number of international suppliers still control the prices of materials for antioxidant stabilizers in the world market.

The market of antioxidant stabilizer additives, especially heat stabilizer in India and Asia Pacific, is growing rapidly. Dedicated antioxidant stabilizers grow with the growth of applications and technological developments of polymer materials. Now, automotive industry, organic electronics, agriculture, film, plastics, rubber, fiber, computer materials and other industries need specific dedicated antioxidant additives and stabilizers to expand the use of these materials and applications.

Demand for antioxidant stabilizers is also widely used in plastics industry, particularly the development in the field of olefins, chlorinated polymers (PVC). PVC products are mainly used in the construction field, especially for pipes and cable manufacturing. More than 85% of the antioxidant additives are used in this industry. Demand for the Asia-Pacific region is expected to grow further. Light antioxidant additives will grow more rapidly. Especially, the increase for polypropylene and polyethylene products will be greater.

Most of polymer material needs to be processed or treated at temperatures above 200° C. The material tends to have issues like shorter life, fading colors, weakened strength, or brittle/cracking surfaces and the like due to continuously subjected to high temperature and strong light condition. However, introducing specific antioxidant stabilization additives can prevent from these issues and reduce material damage, prolong material life, maintain aesthetics and durability, reduce costs, decrease waste production, and protect the environment.

Currently, antioxidant stabilizer additives used on the market have low molecular weights, high volatility or loss for degradation, uneven distribution of effects in materials. Thus, the issues such as short life, color damage, weakened strength or embrittlement or cracking occur due to being damaged during the processing or utilization of materials, especially under high temperatures and strong light conditions.

It is reported on articles regarding multifunctional antioxidant stabilizers within light-resistant and heat resistant molecules that some international companies have begun to design and produce such products. The data showed that this kind of multifunctional antioxidant provides much better synergistic effects than two kinds of antioxidants used in combination.

The macromolecular anti-oxidation stabilizer and its preparation method and application, designed and developed by the inventors have overcome the above problems so that the corresponding material can maintain stable properties under high temperature and strong light irradiation conditions. The invention is thus produced.

BRIEF SUMMARY OF INVENTION

In view of the technical problems of the prior art, the objective of the present invention is to provide a multifunctional synergistic macromolecular anti-oxidation stabilizer, and its manufacturing method and applications.

To achieve the above-mentioned objective, the present invention is carried out by the following technical solutions: A multifunctional synergistic multifunctional synergistic macromolecular anti-oxidation stabilizer having the following formula:

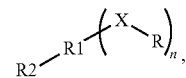

wherein R1 is a connection chain which is a fatty chain, an aromatic structural chain or a fatty and aromatic structurally combined chain;
R2 is

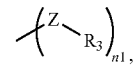

X is O, S, N or NH, or —CONR—, Z is O, S, N or NH, and X is different from Z; R is a fatty chain, an aromatic group, a sterically hindered amine or a sterically hindered phenol, R3 is a fatty chain, an aromatic group, a sterically hindered amine or a sterically hindered phenol, R is identical to R3, or R is different from R3;
n is a positive integer including 1, n1 is a positive integer including 1, n is identical to n1, or n is different from n1.

The multifunctional synergistic macromolecular anti-oxidation stabilizer is:

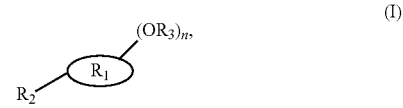

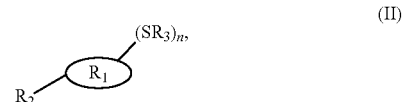

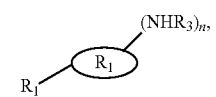
(III-1)
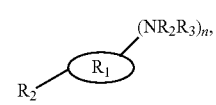
(III-2)
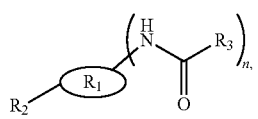
(IV-1)
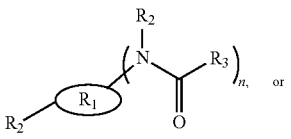
(IV-2)
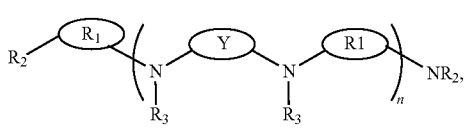
(V)
the R3 is H, an aliphatic side chain, an aromatic side chain, a mixed aromatic/aliphatic side chain, or a side chain having heteroatoms; n is a positive integer.
As exemplary structures of such anti-oxidation stabilizer, the anti-oxidation stabilizer is:
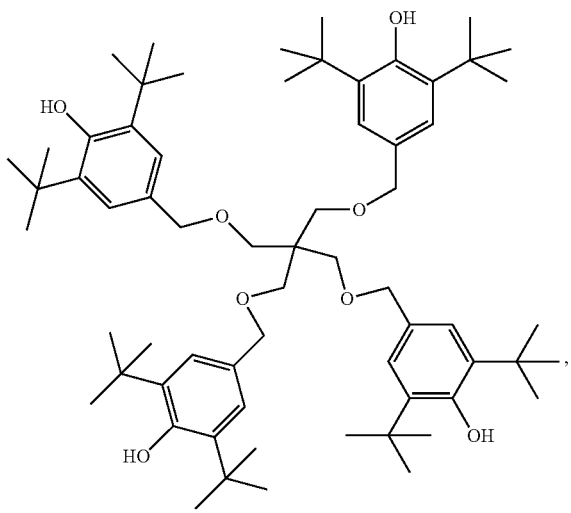 [SMILES: CC(C)(C)c1cc(COCC(COCc2cc(C(C)(C)C)c(O)c(C(C)(C)C)c2)(COCc2cc(C(C)(C)C)c(O)c(C(C)(C)C)c2)COCc2cc(C(C)(C)C)c(O)c(C(C)(C)C)c2)cc(C(C)(C)C)c1O]
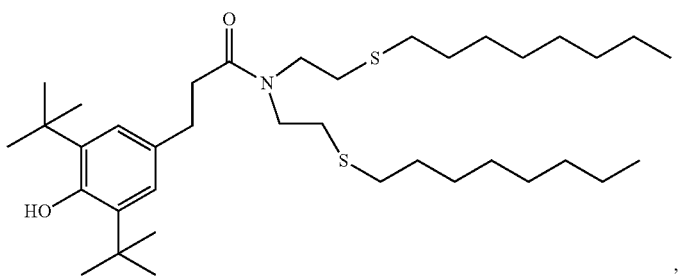 [SMILES: CCCCCCCCSCCN(CCSCCCCCCCC)C(=O)CCc1cc(C(C)(C)C)c(O)c(C(C)(C)C)c1]
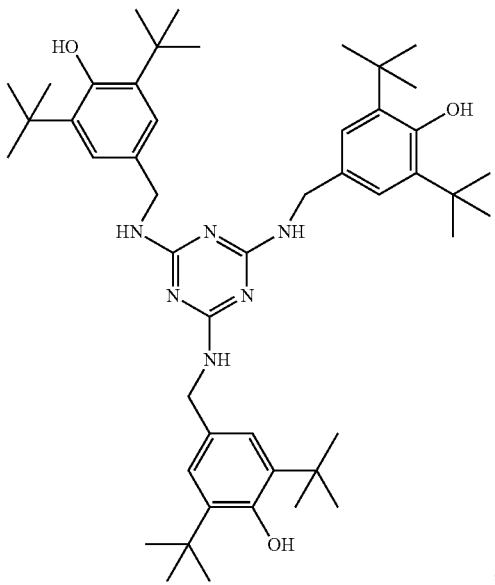

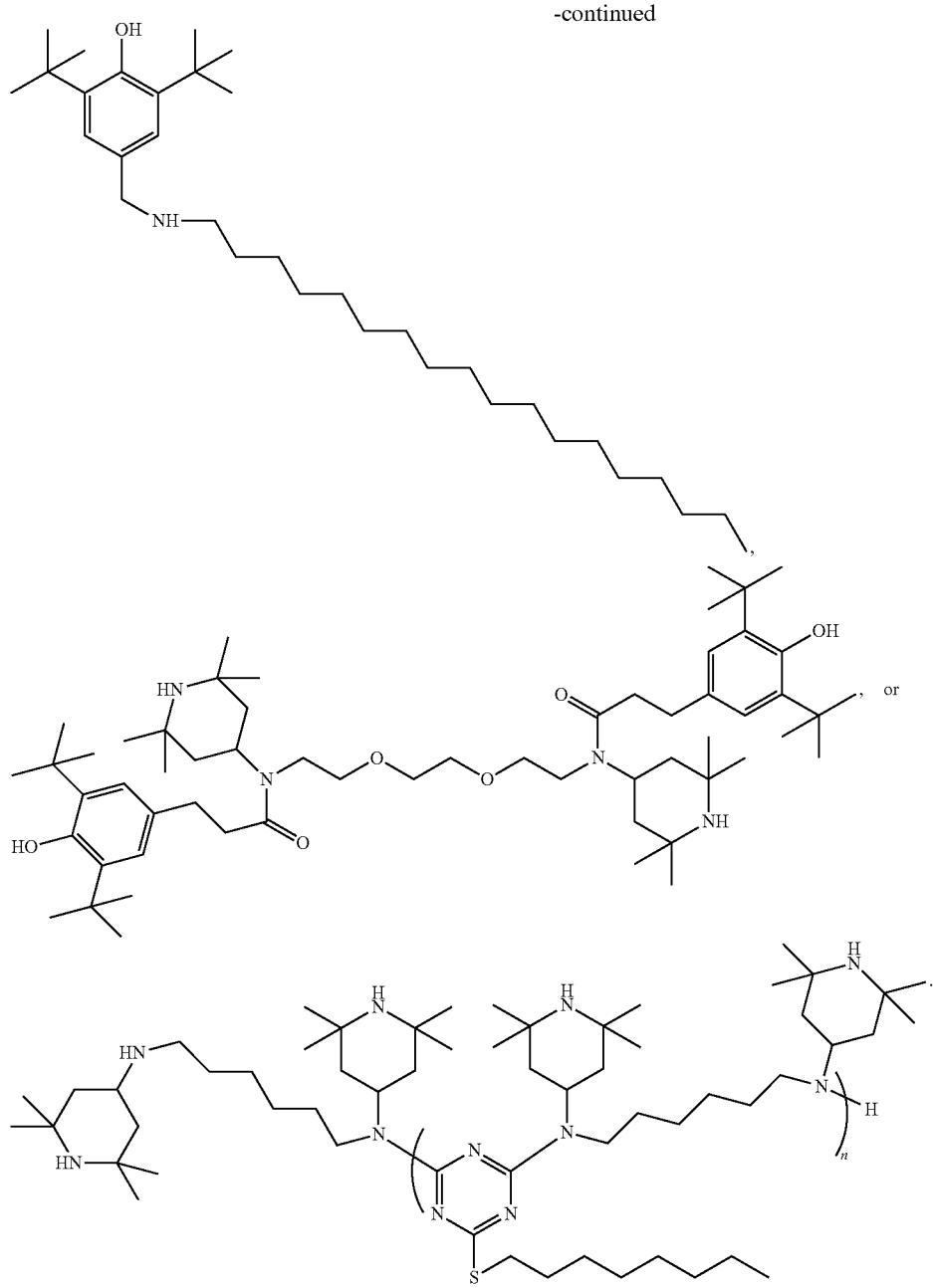

A method of preparing multifunctional synergistic macromolecular anti-oxidation stabilizer, comprising steps of:

n is an integer which is >1 adding 1 equivalent of alcoholic raw material to a solvent which is anhydrous THF, DMF, acetone, ethyl acetate, toluene or acetonitrile and containing 1.5-5 equivalents of NaH (1:5-15, w/v) under nitrogen, stirring for 30 minutes to 1 hour at room temperature or at 30-50° C. along with synchronously heating, adding dropwise 1.2-5.0 equivalents of iodides, bromides or chlorides with 10% NaI or KI, or activated alcohols (e.g., toluene sulfates of alcohols, trifluoroacetate, etc.), stirring the mixtures at room temperature for 30 minutes to 1 hour and heating to 40-90° C., monitoring the reaction by TLC until the reaction is complete; quenching saturated NH$_4$Cl aqueous solution (1-3 times the volume of the reactive organic solvent), adding ethyl acetate or dichloromethane and fully mixing, separating organic phase and extracting aqueous phase three times, drying the organic phase with Na$_2$OS$_4$, filtering and removing the organic solvent in vacuum; obtaining solid product by recrystallization and oil or liquid product by purification through extraction or silica gel column chromatography;

or adding 1 equivalent of alcoholic raw material to a solvent which is THF, acetone, ethyl acetate or acetonitrile, dichloromethane, chloroform, toluene or DMF and containing 1-3 equivalents of NaOH (1:5-20, w/v) and 10-20% tetrabutylammonium bromide under nitrogen protection, stirring for 1 hour to 3 hour at room temperature or at 30-50° C. along with synchronously heating, adding dropwise 1.5-3.0 equivalents of iodides, bromides or chlorides with 10% NaI or KI, or activated alcohols (e.g., toluene sulfates of alcohols, trifluoroacetate, etc.), stirring the mixtures at room temperature for 1 hour, heating to 40-100° C. and reacting for 1-25 hours, monitoring the reaction by TLC until the reaction is complete, obtaining solid product by recrystallization and oil or liquid product by purification through extraction; 83-92% yield;

or adding dropwise 1 equivalent of thiol to dried THF, DCM, acetone, acetonitrile or ethyl alcohol, dichloromethane, chloroform, toluene or DMF containing 1-1.5 equivalents of iodides, bromides or chlorides with 10-20% NaI or KI, or activated alcohols (e.g., toluene sulfates of alcohols, trifluoroacetate, etc.), then adding an inorganic base such as $Na_2CO_3$ or $K_2CO_3$ or an organic base solution with an organic base such as NEt3 or DMAP or DBU (1.2-2.0 equivalents), stirring the mixtures at room temperature for 30 minutes, and then heating to 40-90° C. and stirring for 5-12 hours, monitoring the reaction by TLC until the reaction is complete; adding NaCl saturated aqueous solution and an equal amount of ethyl acetate or dichloromethane to the reaction system, fully mixing, separating organic phase, and washing aqueous phase three times with the same organic solvent, drying the organic phase with $Na_2OS_4$, filtering, removing the organic solvent in vacuum; obtaining solid product by recrystallization, and obtaining oil or liquid product by extraction or silica gel column chromatography; 78-97% yield;

or dissolving 1 equivalent of amine in a solvent which is dichloromethane, ethyl acetate, acetone, acetonitrile, THF, ethanol, methanol, chloroform, toluene or DMF (1:5-20, w/v), stirring under nitrogen and adding dropwise 1-3 equivalents of organic iodides, organic bromides (10-50% NaI, w/w) or organic chlorides (10-50% NaI, w/w), or activated alcohol compounds (MsO-, TsO-, TfO-) to the same organic solvent containing 1-3 equivalents of bases (inorganic or organic bases such as NaOH, KOH, $Na_2CO_3$, $K_2CO_3$, $NEt_3$, DBU, DMAP), adding 10% butyltin bromide at the time of the addition of the inorganic base, stirring for 1 to 3 hours at room temperature, and then heating to 40-90° C. for additional 1-25 hours; cooling, washing alkaline and water-soluble impurities with the aqueous solution of $NH_4Cl$, obtaining solid product in organic phase by recrystallization, and oil or liquid product by purification through extraction or silica gel column chromatography; 67-93% yield.

or dissolving or suspending 1 equivalent of amine and 1 equivalent of base (inorganic base or organic base) in a solvent which is anhydrous dichloromethane, THF, MTBE, acetone, ethyl acetate, acetonitrile, chloroform, toluene or DMF (1:5-20, w/v), adding dropwise a solution of 1-2 equivalents of carboxyl chloride in the same dry solvent (1:5-10, w/v) at 0-10° C. under nitrogen protection. stirring the mixture at 0-10° C. for 30 minutes at room temperature or heating to 30-60° C. and reacting for 3-24 hours, monitoring the reaction by TLC until the reaction is complete; adding (1:20) dichloromethane, ethyl acetate or MTBE and 0.1N iced hydrochloric acid solution, mixing and then isolating organic phase, washing aqueous phase with the same organic solvent twice, drying the organic phase with anhydrous $Na_2SO_4$, filtering, concentrating; obtaining solid product in organic phase by recrystallization, and obtaining oil or liquid product by silica gel column chromatography or extraction; 75-96% yield.

or controlling the average molecular weight of the multifunctional anti-oxidation stabilizer macromolecular product ranging from 1000 to 5000 daltons by adjusting the number of n of multifunctional group in the used raw material.

dissolving 1 equivalent of diamine, polyamine in dry dichloromethane, ethyl acetate, THF, acetone, acetonitrile, ethanol, methanol, chloroform, toluene or DMF (1:5-15, w/v), and then stirring and adding dropwise polyiodinated, polybrominated or polychlorinated organic raw materials under nitrogen protection, (bromine and chloride to be added 10-50% NaI or KI, and the corresponding $Bu_4NBr$), stirring at room temperature for 30 minutes and 1 hour, and then heating to 40-100° C. and reacting for 6-72 hours until precipitate no longer increase; filtering to produce solid powder product (white or light yellow), washing 3 times with dichloromethane; (1;2=w/v), about 87-100% yield.

The polyfunctional raw material may be other polyfunctional starting materials other than polyamines such as polyhydric alcohols, polythiols, polyorganic acids, polyaldehydes, polyacid chlorides and the like.

Reaction themes of a manufacturing method of multifunctional synergistic macromolecular anti-oxidation stabilizer are:

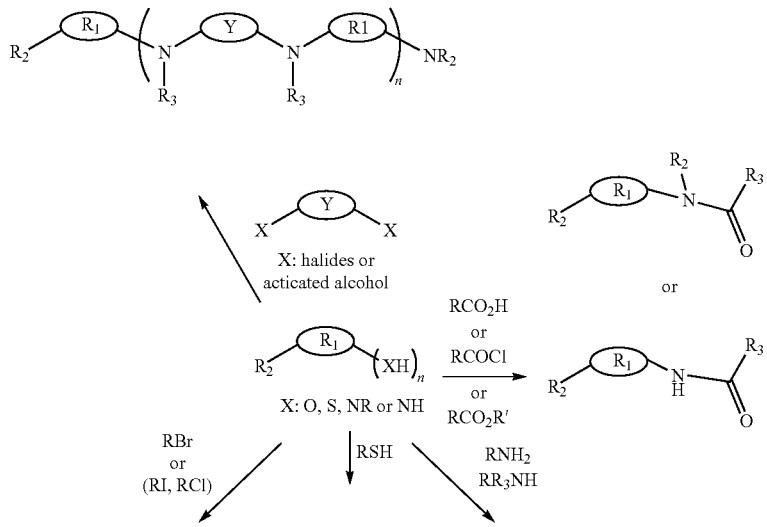

-continued

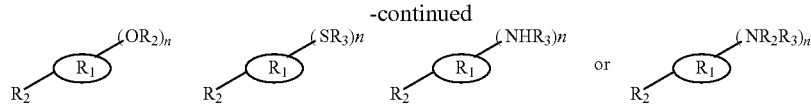

A use of a multifunctional synergistic macromolecular anti-oxidation stabilizer as an antioxidant is provided.

Preferably, a use of the multifunctional synergistic macromolecular anti-oxidation stabilizer in plastics, rubbers, petroleum, coatings, fiber products or painting.

The invention adopts a thioether bond, a secondary amine bond or a tertiary amine bond, and an ether bond as a bridge through a designed link spacer to combine a variety of light-resistant, heat-resistant and processing-resistant antioxidant functional fragments together to form a new type of anti-stabilizer. In one aspect of the invention, the macromolecular anti-oxidation stabilizer.

The macromolecular anti-oxidation stabilizer of the invention can adjust the matching of the anti-oxidation stabilizer and the specific structure of macromolecules by designing the link spacer and substituted side chains, in order to reduce defects in the macromolecules such as migration, leakage and being extracted of conventional anti-oxidation stabilizer. In another aspect, a novel anti-oxidation stabilizer may have a variety of hybrid functional synergistic effects with the types of introduced antioxidant functional groups.

A new heat-resistant and light-resistant antioxidant agent having large molecular weight is produced by designing the link spacer fragment and the side-chain structures, when the introduced antioxidant functional groups are the same type (for example, the main heat-resistant hindered phenol functional fragment, the main light-resistant hindered amine functional fragments). A new multifunctional hybrid synergistic anti-oxidation stabilizer is produced when the introduced antioxidant functional group fragments respectively belong to different types of mechanisms of anti-oxidation (for example, the main antioxidant functional heat-resistant hindered phenol and light-resistant hindered amine, the main antioxidant functional hindered phenol or hindered amine fragments and assistive antioxidant functional fragment thioether and phosphite).

The characteristics of the multifunctional hybrid synergistic anti-oxidation stabilizer are not only combination of different antioxidant properties, but greater superiority of the protection for molecules and the matching of specific macromolecules.

The invention has been developed multifunctional hybrid for the first time, slow release and long acting, and a new type of anti-oxidation stabilizer with resistance against such as hydrolysis, acid, alkali, etc. With a stable ether bond or amine bond or amide bond as a primary light-resistant and heat-resistant hybrid bonding way through the design of appropriate space-controlled conformation to limn anti-oxidation stabilizer acting with multifunctional synergistic effects.

The multifunctional synergistic macromolecular anti-oxidation stabilizer of the invention has advantage due to stably bonded multifunctional hybrid synergistic, heat-resistant, hydrolysis-resistant, acid-resistant and base-resistant and other properties, and to make up for the weakness of similar products in the today's market and to lay the foundation for the development of a new generation of effective anti-oxidation stabilizers.

DETAILED DESCRIPTION OF EMBODIMENTS

The present invention will now be described in further detail with reference to specific embodiments, but the scope of the present invention is not limited thereto.

Example 1

1. Formula

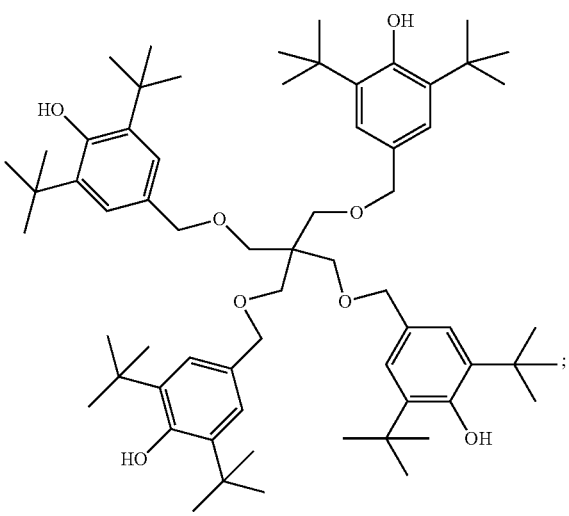

2. Synthetic Routes

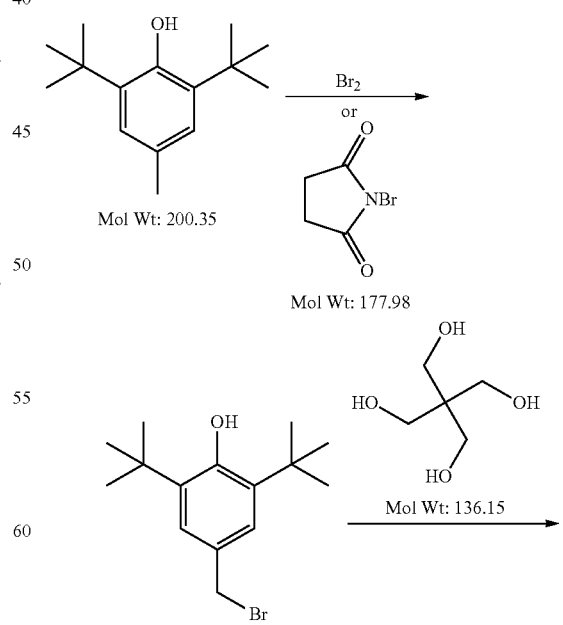

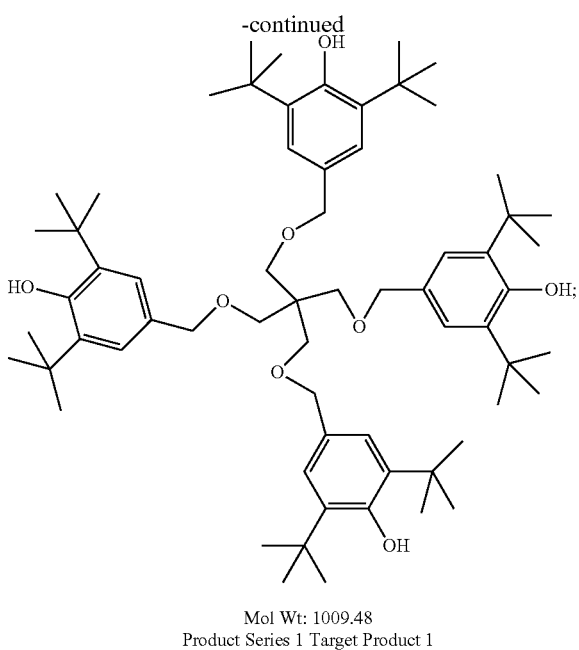

Mol Wt: 1009.48
Product Series 1 Target Product 1

3. Step 1 of the Synthesis of 4-bromomethyl-2,6-di-tert-butyl phenol (Intermediate 1)

5 g of 2,6-di-tert-butyl-p-cresol (22.69 mmol) was dissolved in a solvent such as $CCl_4$ or $CHCl_3$ or dichloromethane or THF or toluene or DMF (20-50 ml). A solution of liquid bromine (1.2-1.5 mmol) was added dropwise to the solvent above (15-50 ml) under nitrogen protection and UV lamp (350 watts of mercury lamp) irradiation. The rate of dropwise adding varied depending on the reaction rate. The reaction was monitored by TLC. Oily product was obtained by stirring for 5-20 minutes after the end of the titration and removing the organic solvent in vacuum, which was used directly in the next step.

4. Step 2 of the Synthesis of 4-bromomethyl-2,6-di-tert-butyl phenol (Intermediate 1)

5.0 g of 2,6-di-tert-butyl-p-cresol (22.69 mmol) was dissolved in a solvent such as CCl4 or CHCl3 or THF or chlorobenzene (25-50 ml), and added dropwise to a solution of 4.1 g of NBS (22.90 mmol) containing 3-10% benzoyl peroxide of the same solvent (20-60 ml). The mixture was refluxed for 2-5 hours and cooled to room temperature. The solid suspension was filtered off. Light brown liquid is obtained by removing the organic solvent in vacuum, which was used directly in the next step.

5. Preparation of Target Product 1

2 g of pentaerythritol (1.98 mmol), potassium hydroxide or sodium hydroxide (11.89 mmol) and tetrabutylammonium bromide (0.5 mmol) were dissolved in 20 ml of THF or acetonitrile or acetone or DMF. The mixture was stirred at room temperature for 1 hour and heated to 50-70° C. for 30 minutes to hours, and cooled to room temperature. 3.49 g of 2,6-di-tert-butyl-4-bromomethylbenzene (15.45 mmol) under nitrogen. The mixture was refluxed for 18 hours and the reaction was monitored by TLC until the starting material of pentaerythritol disappeared and had a major product point formed. 0.1N iced hydrochloric acid solution and the same volume of dichloromethane or ethyl acetate was added. Organic phase was separated after fully mixing. Aqueous phase was washed with the same solvent. The organic phase was dried with anhydrous $Na_2SO_4$. Target Product 1 was obtained by filtering, removing organic solvent in vacuum and purification through silica gel column chromatography, 83.7% yield.

$^1H$ NMR (400 MHz, $CHCl_3$), δ (ppm): 7.26 (s, $CHCl_3$ in $CDCl_3$), 7.15 (s, 2H, 2CH), 7.00 (s, 2H, 2CH), 6.92 (s, 2H, 2CH), 6.87 (s, 2H, 2CH), 6.66 (s, 4H, 2CH2), 5.62 (s, 4H), 3.17 (s, 4H, 2CH2), 2.29 (s, 4H, $2CH_2$), 2.26 (s, 4H, $2CH_2$), 1.22-1.43 (m, 72H, $24CH_3$).

Example 2

1. Formula:

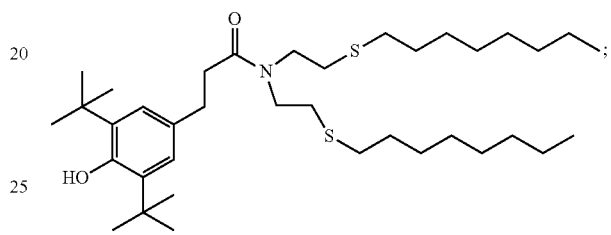

2. Synthetic Routes:

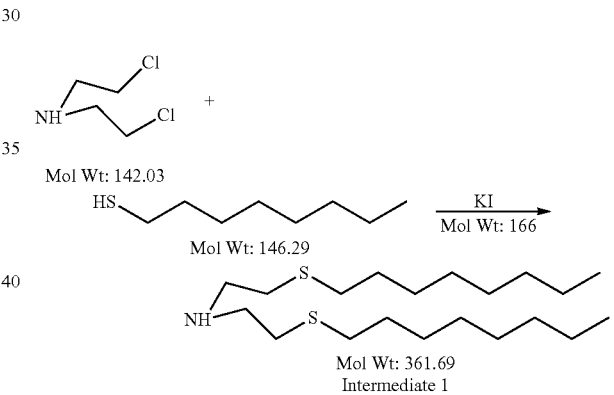

Mol Wt: 361.69
Intermediate 1

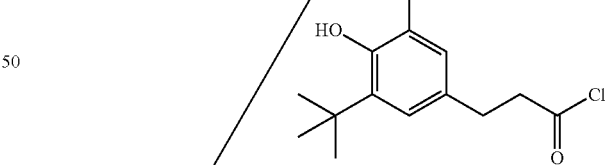

Intermediate 2
Mol Wt: 296.83

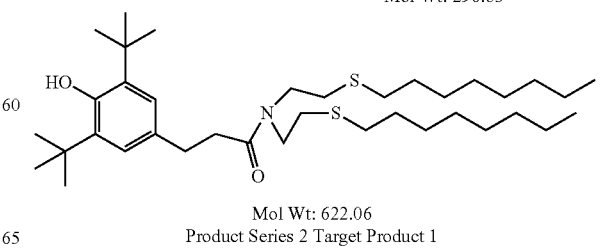

Mol Wt: 622.06
Product Series 2 Target Product 1

3. Predation of Intermediate 1

6.1 g of thiol (42.30 mmol) was added dropwise in a solution such as THF or acetone or acetonitrile or dichloromethane or ethanol containing 2,2-dichloroethylamine (21.12 mmol) and 10-50% KI (1:5-20, w/v). The mixture was heated to 40-90° C., reacted for 3-9 hours. The reaction was monitored by TLC until the reaction was completed. The organic solvent was removed in vacuum.

NaCl aqueous solution and dichloromethane or ethyl acetate were added, to fully mixed, the organic phases were separated the same volume of dichloromethane or ethyl acetate was added and fully mixed. The organic phase was separated, and the aqueous phase was extracted twice. The organic phase was dried with Na$_2$SO$_4$. Intermediate 1 was obtained by filtering and concentrating, which was used directly in the next step.

4. Preparation of Intermediate 2

5.93 g of 3-(3,5-di-tert-butyl-4-hydroxybenzene) propionic acid (21.30 mmol) was dissolved in dry THF or dichloromethane or ethyl acetate or MTBE or acetone (1:5-20, w/v). After cooling to 0-10° C., 1.82 ml of oxalyl chloride (21.50 mmol) and 0.5 ml of dropping DMF were added dropwise under nitrogen, and the mixture was stirred for 30 minutes. The temperature was raised to room temperature and the mixture was stirred for 2-7 hours. The reaction was monitored by TLC until the reaction was complete. The organic solvent and excess oxalyl chloride were removed in vacuum and the remaining Intermediate 2 was used directly in the next step.

3. Preparation of Target Product 1:

Intermediate 1 (21.12 mmol) and Intermediate 2 (21.30 mmol) were dissolved in dry organic solvents such as acetone or THF or ethyl acetate or ethyl cyanide or toluene or methylene chloride, cooled to 0-10° C. Ethylamine (21.30 mmol) was added dropwise and the mixture was stirred at 0-10° C. for 1 hour and then at room temperature for 3-7 hours. The reaction was monitored by TLC until the reaction was complete. 0.1N of iced hydrochloric acid aqueous solution and the same volume of dichloromethane or ethyl acetate were added to the reaction system. The organic phase was separated and the organic phase was washed twice with 0.1N iced hydrochloric acid aqueous solution and twice with saturated NaCl solution, and dried with anhydrous Na$_2$SO$_4$. 9.87 g of Target Product 1 was obtained by filtering, removing organic solvent in vacuum, and purification through silica gel column chromatography, 75.1% yield.

$^1$H NMR (400 MHz, CDCl$_3$), δ (ppm): 7.25 (s, CHCl$_3$, from CDCl$_3$), 6.97 (s, 2H, 2CH), 2.76-2.99 (m, 8H, 4CH$_2$), 1.52-1.59 (m, 4H, 2CH$_2$), 1.43 (s, 18H, 2Bu$^t$), 1.26-1.43 (m, 24H, 12CH$_2$), 0.88 (t, 6H, $^3J_{HH}$=7.20, 2CH$_3$).

Example 3

1. Formula

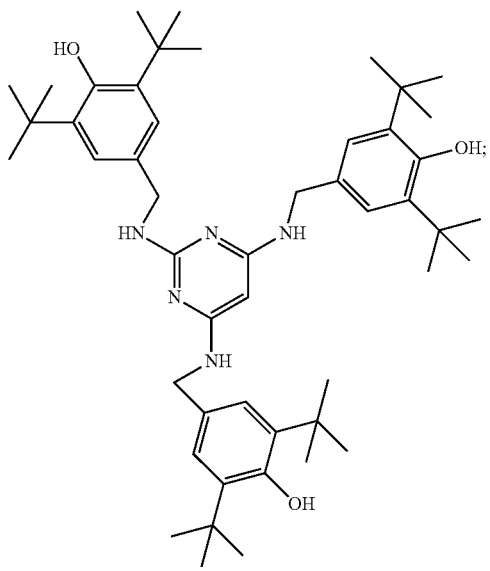 [SMILES: CC(C)(C)c1cc(CNc2cc(NCc3cc(C(C)(C)C)c(O)c(C(C)(C)C)c3)nc(NCc3cc(C(C)(C)C)c(O)c(C(C)(C)C)c3)n2)cc(C(C)(C)C)c1O]

2. Synthetic Route

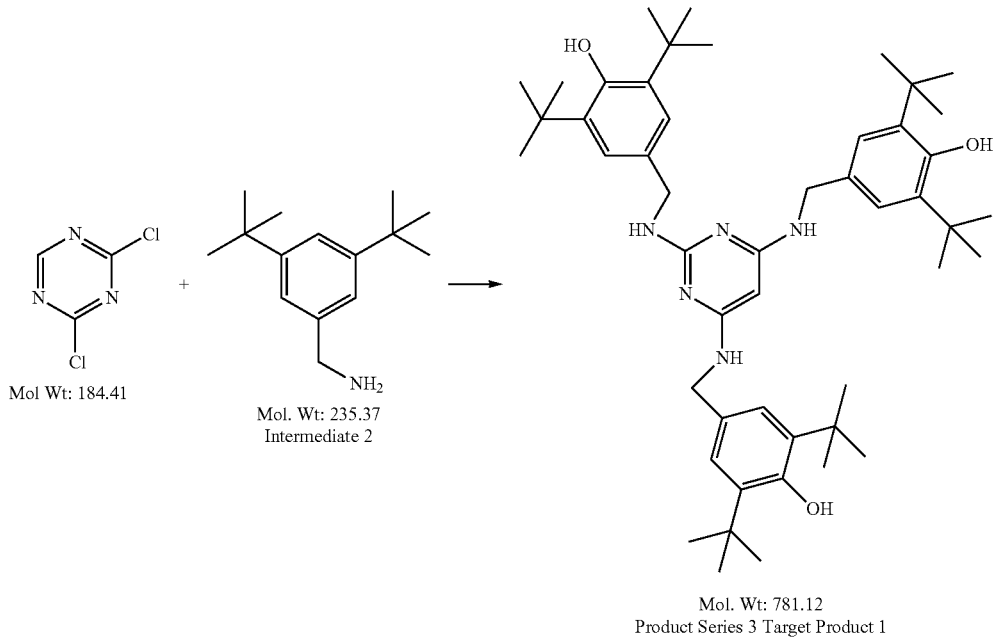

Mol. Wt: 781.12
Product Series 3 Target Product 1

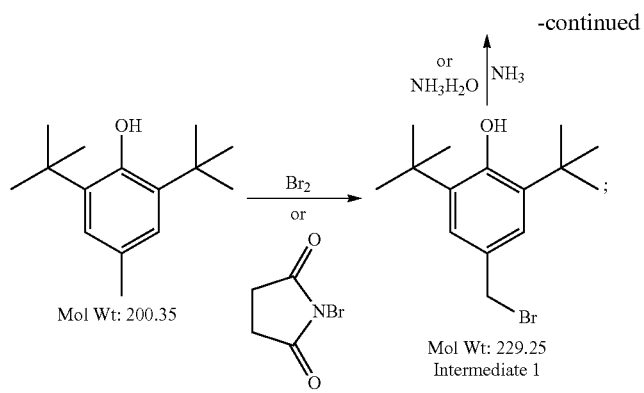

3. Step 1 of the Synthesis of 2,2,6,6-di-tert-butyl-4-bromomethylphenol (Intermediate 1)

5 g of 2,2,6,6-di-tert-butyl-p-cresol (27.11 mmol) was dissolved in a solvent such as CCl$_4$ or CHCl$_3$ or CH$_2$Cl$_2$ or THF or chlorobenzene or toluene or dibromoethane (1:5-20, w/v). A solution of bromine (28.01-37.57 mmol) in the same volume of solvent was added dropwise with 350 watts of mercury lamp under nitrogen protection. The reaction was monitored by TLC. After completion of the dropwise addition, the mixture was stirred for 5 to 40 minutes and the organic solvent was removed in vacuum to give a pale reddish brown oil which was used directly in the next reaction, 95-100% yield.

4. Step 2 of the Synthesis of 2,2,6,6-di-tert-butyl-4-bromomethyl phenol (Intermediate 1)

5 g of 2,2,6,6-di-tert-butyl-p-cresol (27.11 mmol) was dissolved in CCl4 or CHCl$_3$ or CH$_2$Cl$_2$ or THF or chlorobenzene or toluene or dibromoethane solvent (1:5-20, w/v), 3-10% benzoyl peroxide was added, heated to reflux, and 6.3 g of NBS (35.25 mmol) was added dropwise into the solution with the same volume and the same solvent, and refluxed for 2-5 hours after dropwise addition. The mixture was cooled to room temperature, filtered to a suspended solid, and the filtrate was concentrated in vacuum to give a pale red oil which was used directly in the next step, 90-95% yield.

5. Step of the synthesis of 2,2,6,6-di-tert-butyl-4-aminomethylphenol (Intermediate 2)

3 grams of 2,2,6,6-di-tert-butyl-4-bromomethylphenol was dissolved in THE or acetone or ethanol or methanol and other solvents, ammonia or ammonia air was added and reacted for 2-6 hours at room temperature. The reaction was monitored by TLC until benzyl bromide disappeared.

Dichloromethane or petroleum ether or ethyl acetate or toluene or MTBE was added to extract the benzylamine product into the organic phase (10 ml×3). The combined organic phases were dried with anhydrous Na$_2$SO$_4$ and filtered. The filtrate was removed in vacuum to remove the organic solvent. A pale yellow waxy solid was obtained which was used directly in the next step, 81-93% yield.

6. Preparation of Target Product 1

1 g of cyanuric chloride (5.42 mmol) was dissolved in anhydrous dichloromethane or THF or MTBE or ethyl acetate or ethanol or a solvent such as acetone or DMF (1: 5-20, w/v). 5.75 g of Na$_2$CO$_3$ (5.42 mmol) and the above-prepared crude benzylamine (21.68 mmol) were added under nitrogen protection. The mixture was stirred at room temperature for 1 hour, heated to 40-80° C. for 2-18 hours, and the reaction was monitored by TLC until the reaction was completed. The NaCl aqueous solution was added, the organic phase was extracted with dichloromethane or ethyl acetate (10 ml×3) and dried with anhydrous Na$_2$SO$_3$. The organic phase was filtered, concentrated in vacuum. 3.18 g of white solid was obtained by silica gel chromatography, 75.2% yield.

$^1$H NMR (400 MHz, CDCl3), δ (ppm): 7.31 (t, 3H, 3CH), 7.30 (s, CHCl$_3$ from CDCl$_3$), 7.18 (t, 3H, 3CH), 2.35 (s, 6H, 3CH$_2$), 1.31 (s, 54H, 18CH$_3$).

Example 4

1. Formula:

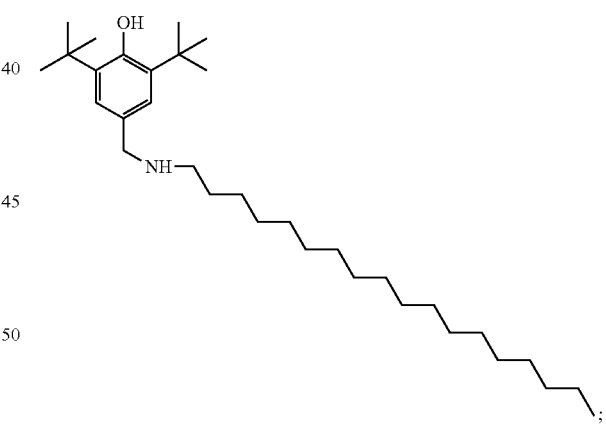

2. Synthetic Route:

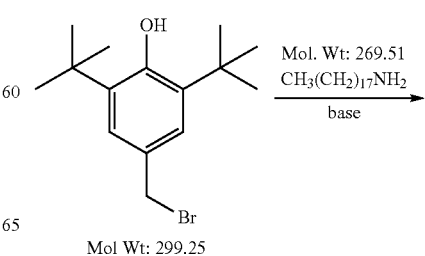

-continued

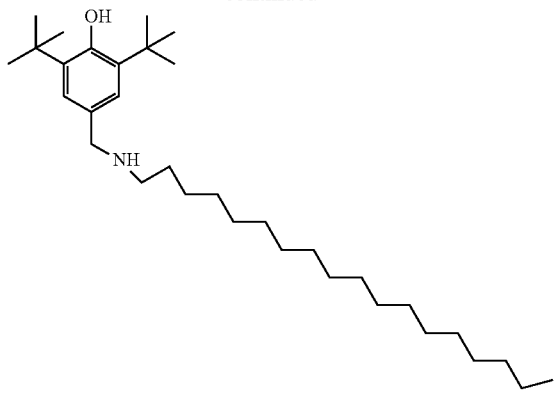

Mol. Wt: 487.84
Product Series 3 Target Product 2
Mol. Wt: 781.12

3. Preparation of Target Product 2:

g of 2,2,6,6-di-tert-butyl-4-bromomethylphenol (3.342 mmol) was dissolved in dichloromethane or ethyl acetate or petroleum ether or THF or MTBE or a solvent such as acetone or ethanol (1:5-20, w/v), and then the solution was added dropwise to a solution of N-octadecylamine and $K_2CO_3$ or $Na_2CO_3$ or NaOH or triethylamine or DBU or DMAP in the same volume and the same solvent. The mixture was stirred at room temperature for 1-5 hours, the reaction was monitored by TLC until the reaction was complete. NaCl aqueous solution was added. The solvent such as dichloromethane or ethyl acetate or MTBE or petroleum ether was used for extraction (10 ml.times.3). A yellowish oil was obtained by silica gel chromatography after filtering and removing the organic solvent, 83-92% yield.

$^1$H MNMR (400 MHz, CDCl3), δ (ppm): 7.34 (s, $CHCl_3$ from $CDCl_3$), 7.15 (s, 2H, 2CH), 3.45 (m, 2H, $CH_2N$), 2.76 (m, 2H, $CH_2N$), 1.13-1.49 (m, 52H).

Example 5

1. Formula:

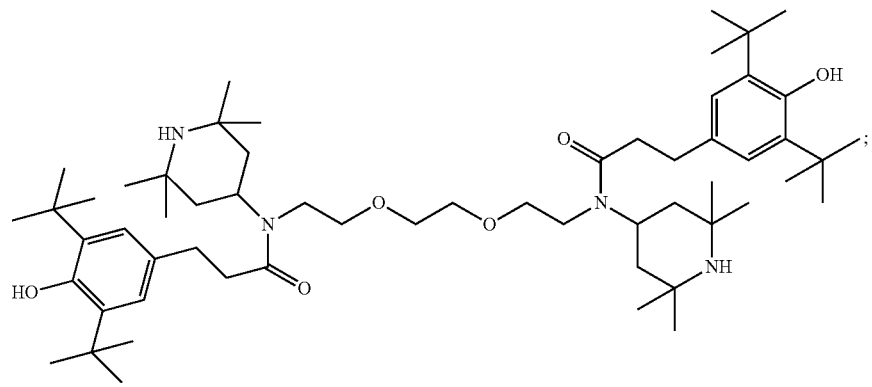 [SMILES: CC1(C)CC(N(CCOCCOCCN(C(=O)CCc2cc(C(C)(C)C)c(O)c(C(C)(C)C)c2)C2CC(C)(C)NC(C)(C)C2)C(=O)CCc2cc(C(C)(C)C)c(O)c(C(C)(C)C)c2)CC(C)(C)N1]

2. Synthetic Route:

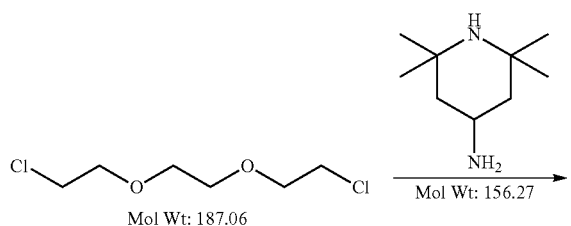

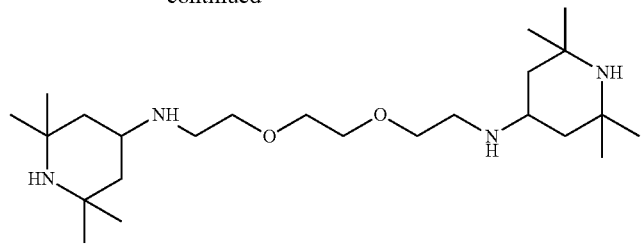

Mol Wt: 426.68
Intermediate 1

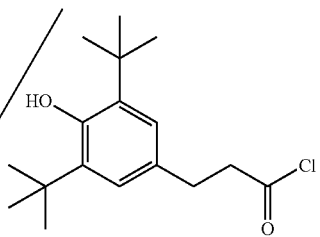

Mol Wt: 296.83
Intermediate 2

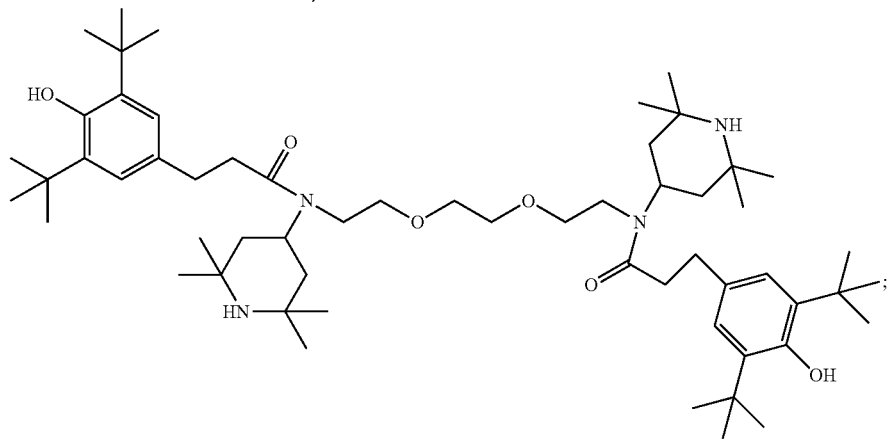

Mol Wt: 947.42
Product Series 4 Target Product 1

3. Synthesis of Intermediate 1:

6 g of 1,2-dichloroethoxyethane (32.08 mmol) was dissolved in a solvent which is acetone or ethyl cyanide or toluene or ethanol or MTBE (1:5-20, w/v). 10-20% NaI or KI or 32.08 mmol of organic or inorganic bases such as Na$_2$CO$_3$ or K$_2$CO$_3$ or NEt$_3$ or DBU or NaOH and 10.16 g of 4-amino-2,2,6,6-tetramethylpiperidine (65.00 mmol) were added to a solution with the same volume and the same solvent. The mixture was heated to 40-70° C. and stirred for 3-18 hours. The reaction was monitored by TLC, and the mixture was cooled to room temperature. NaCl aqueous solution was added. Dichloromethane or ethyl acetate or MTBE or petroleum ether was used to extract Intermediate 1 three times (20 ml.times.3). The organic phase was dried with Na$_2$SO$_4$. Intermediate 1 as light yellow powder was obtained by silica gel chromatography after filtering and concentrating the filtrate, 81-92% yield.

4. Synthesis of Intermediate 2:

5.93 g of 3-(3,5-di-tert-butyl-4-hydroxybenzene) propionic acid (21.30 mmol) was dissolved in dry THF or dichloromethane or ethyl acetate or MTBE or acetone (1:5-20, w/v). The mixture was cooled to 0-10° C. 1.82 ml of oxalyl chloride (21.50 mmol) and 0.5 ml of dropping DMF were added dropwise under nitrogen, stirred for 30 minutes, and the mixture was heated to room temperature for 2 to 7 hours. The reaction was monitored by TLC until the reaction was complete. The organic solvent and excess oxalyl chloride were removed in vacuum and the remaining Intermediate 2 was used directly in the next step.

5. Preparation of Target Product 1:

3 g of Intermediate 1 (7.06 mmol) and 7.36 mmol of a base such as Na$_2$CO$_3$ or K$_2$CO$_3$ or NEt$_3$ or DMAP or DBU were dissolved in a solvent such as anhydrous acetone or THF or dichloromethane or ethyl cyanide or ethyl acetate and cooled to 0° C. 14.25 mmol of Intermediate 2 was added dropwise into a solution with the same volume and the same solvent. After completion of the dropwise addition, the mixture was stirred at 0-10° C. for 30 minutes and at room temperature for 1-3 hours, heated to 40-60° C. for an additional 2-5 hours. The insoluble material was filtered and the filtrate was concentrated to remove the general solvent. The same volume of petroleum ether was added and the mixture was cooled to 0° C. with stirring. 4.79 g of the precipitated white solid was collected, 71.7% yield.

$^1$H NMR (400 MHz, DMSO-D6), δ (ppm): 6.92 (s, 2H, 2CH), 6.89 (s, 2H, 2CH), 6.75 (s, CH$_2$Cl$_2$, solvent), 4.01 (m, 4H, 2OCH$_2$), 3.58 (sb, H$_2$O), 3.41 (m, 4H, 2OCH$_2$), 2.71 (m, 6H, 2NCH$_2$, 2NCH), 2.50 (m, DMSO from DMSO-d$_6$), 2.42 (m, 4H, 2CH$_2$), 2.26 (m, 4H, 2CH$_2$), 1.59 (m, 4H), 0.93-1.48 (m, 64H).

Example 6

1. Formula:

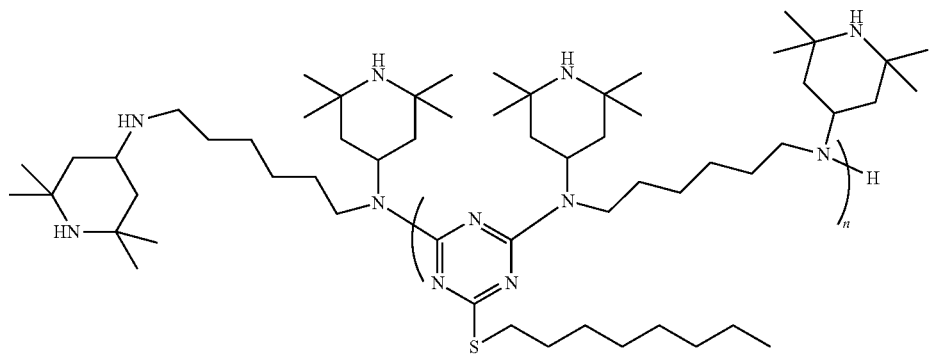

2. Synthetic Route:

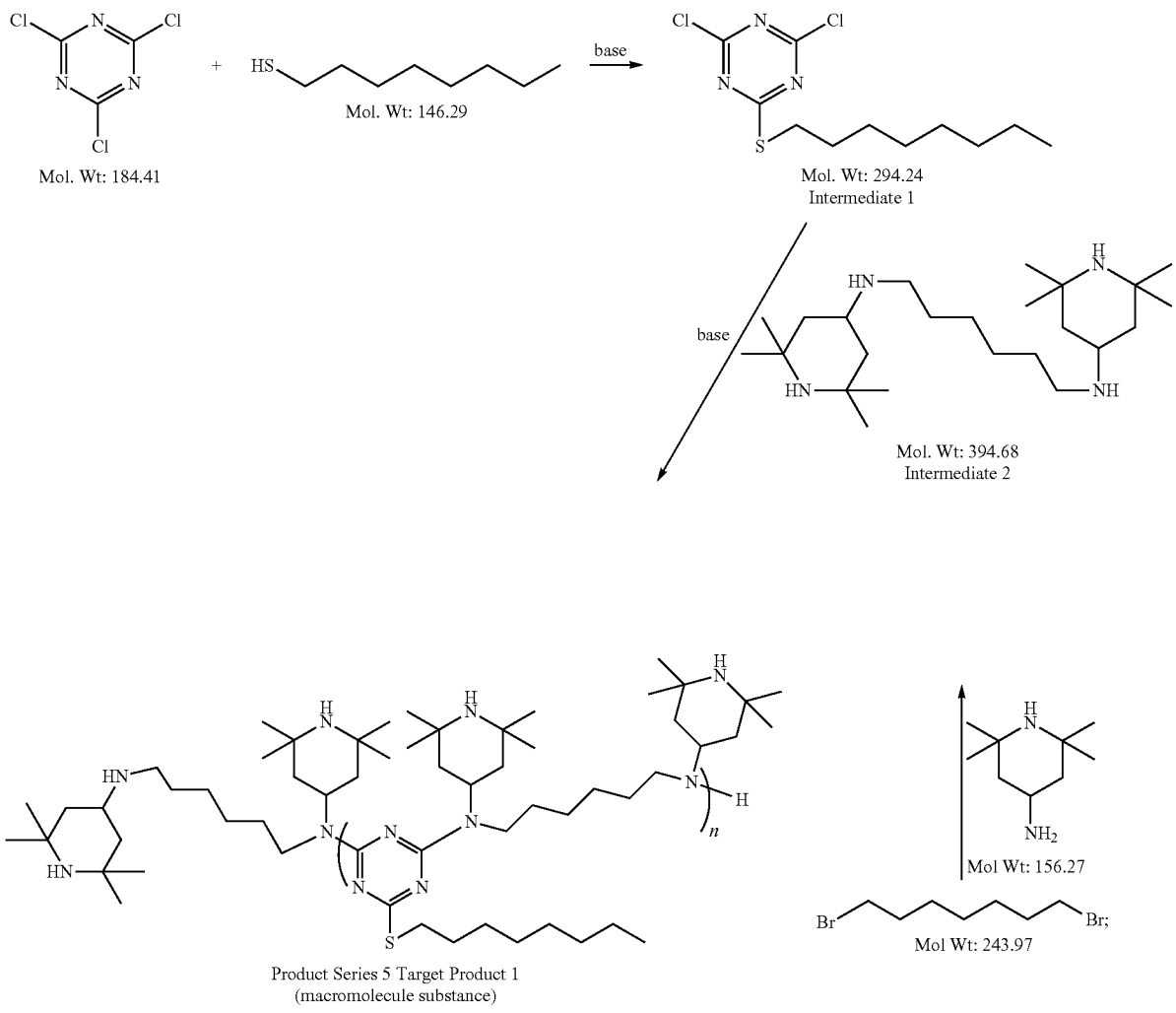

Product Series 5 Target Product 1 (macromolecule substance)

3. Synthesis of Intermediate 3

1 g of cyanuric chloride (5.42 mmol) and 5.42 mmol of Na$_2$CO$_3$ or K$_2$CO$_3$ or NEt$_3$ or DBU or DMAP were dissolved in dry solvent such as acetone or dichloromethane or acetonitrile or THF or toluene. 1.03 g of octanethiol (7.05 mmol) was added under nitrogen protection. The mixture was stirred at room temperature for 1 hour and heated to 35-65° C. for 2-7 hours. The reaction was monitored by TLC until the reaction was complete. This reaction was used directly in the next step.

4. Synthesis of Intermediate 2:

3 g of 1,6-dibromohexane (12.30 mmol), 10-30% NaI or KI and 25 mmol of base such as Na$_2$CO$_3$ or K$_2$CO$_3$ or NEt$_3$ or DBU or DMAP were dissolved in a solvent such as dichloromethane or acetone or THF or MTBE or acetonitrile or toluene or ethanol (1:7-20, w/v).

3.88 g of 4-amino-2,2,6,6-tetramethylpiperidine (24.80 mmol) was added at room temperature. The mixture was stirred at room temperature for 1 hour and heated to 40-70° C. for 3-15 hours. The reaction was monitored by TLC until the reaction was completed. NaCl aqueous solution was added, and dichloromethane or ethyl acetate or MTBE was used for extracting Intermediate 2 (15 ml×3). The combined organic phases are dried with MgSO$_4$. The crude product Intermediate 2 was obtained by filtering and removing the organic solvent, and used directly in the next step.

5. Preparation of Target Product 1 (Macromolecular Substance)

The equimolar Intermediate 2 was added to the reaction system of the equimolar Intermediate 1 while equimolar organic or inorganic bases such as Na$_2$CO$_3$ or K$_2$CO$_3$ or NEt3 or DBU or DMAP was added. The mixture was reacted and stirred at room temperature for 1 hour, and then heated to 50-90° C. and stirred for 5-18 hours. The high molecular weight of the product could be adjusted with the heating temperature and the reaction time. The mixture was cooled to room temperature and the iced aqueous solution was added thereto to wash water-soluble impurities. An oil which was dissolved in an organic solvent could be obtained, a waxy solid could be obtained, and a white solid product could be obtained as Target Product 1, 73-91% yield.

$^1$H NMR (400 MHz, CDCl3), δ (ppm): 7.32 (s, CHCl$_3$ from CDCl$_3$), 4.86 (m, 2H, 2CHN), 3.41 (m, 2H, 2CHN), 3.05 (m, 8H, 4CH$_2$N), 1.98 (m, 2H, CH$_2$S), 1.67 (m, 8H), 1.11-1.49 (m, 63H).

The foregoing examples are merely illustrative of the inventive concept of the invention and are not to be construed as limiting the scope of the invention, and any substantial changes to the invention may be made without departing from the scope of the invention.

What is claimed is:

1. A multifunctional synergistic polymer anti-oxidation stabilizer, which is characterized by the following formula:

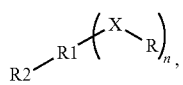

wherein R1 is a connection chain which is a aliphatic chain, an aromatic structural moiety or a alkyl and aromatic structurally combined chain;

R2 is

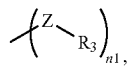

X is O, S, NR or NH, or —CONR—, Z is O, S, NR or NH, and X is different from Z;

R is a alkyl chain, an alkenyl chain, an aromatic group, a sterically hindered amine or a sterically hindered phenol, R3 is a alkyl chain, an aromatic group, a sterically hindered amine or a sterically hindered phenol, R is identical to R3, or R is different from R3;

n is a positive integer including 1, n1 is a positive integer including 1, n is identical to n1, or n is different from n1;

when the stabilizer is of the formula:

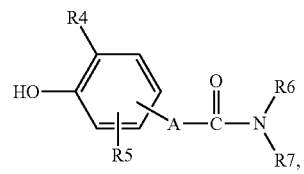

R6 and R7 are both bulky groups having at least 8 carbon atoms, and include aliphatic sulfide.

2. The multifunctional synergistic polymer anti-oxidation stabilizer as claimed in claim 1, wherein —X—R in the multifunctional synergistic polymer anti-oxidation stabilizer is —(OR3)n, —(SR3)n, (NHR3)n or —(NR2R3)n, or wherein —X—R is

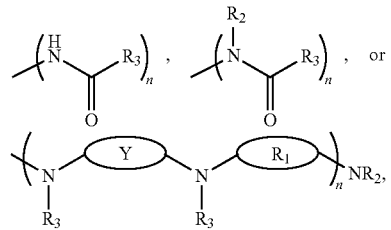

the formula turned into as the following formula:

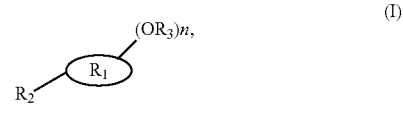 (I)

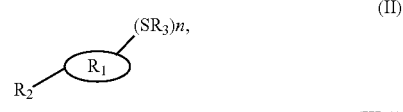 (II)

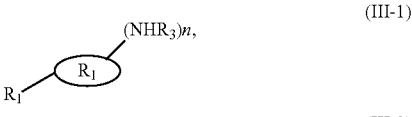 (III-1)

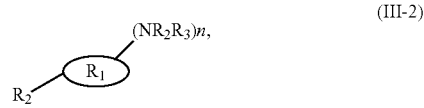 (III-2)

-continued

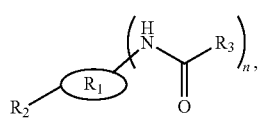
(IV-1)

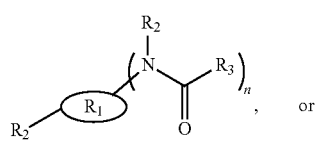
(IV-2)

, or

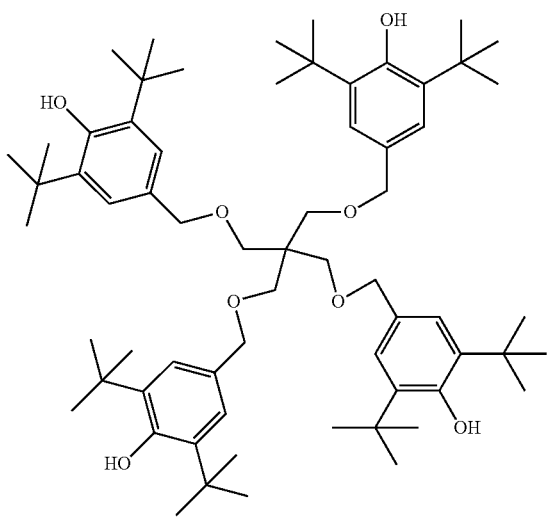

(V)

the R3 is H, an aliphatic side chain, an aromatic side chain, a mixed aromatic/aliphatic side chain, or a side chain having heteroatoms including S, O, N; n is a positive integer.

3. The multifunctional synergistic polymer anti-oxidation stabilizer as claimed in claim 2, wherein example structures of the multifunctional synergistic polymer anti-oxidation stabilizer is;

,

,

-continued

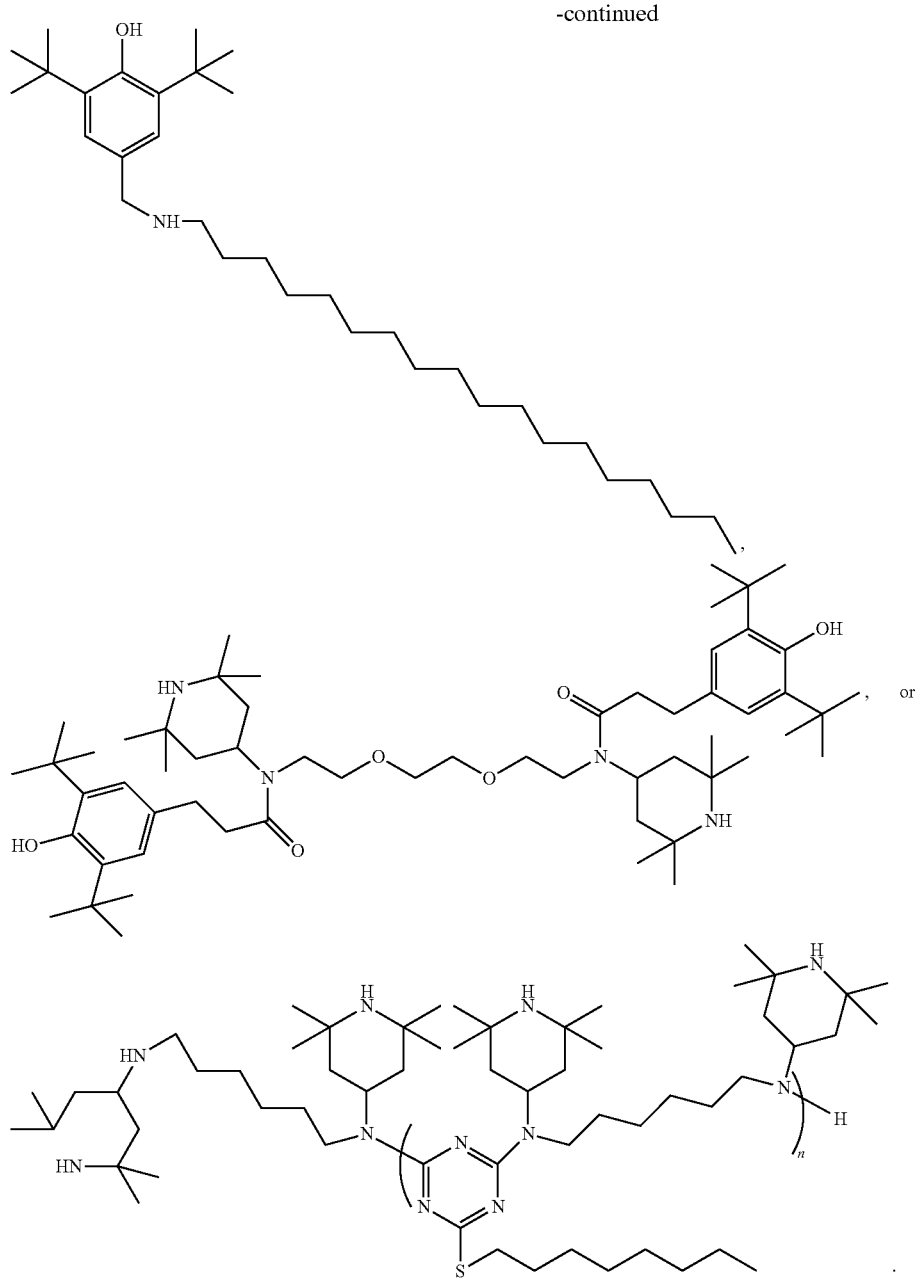

4. A method for preparing the multifunctional synergistic polymer anti-oxidation stabilizer as claimed in claim 2, which is characterized by comprising steps of:

n is an integer which is ≥1, adding 1 equivalent of alcoholic raw material to a solvent which is anhydrous THF, DMF, acetone, ethyl acetate, toluene, MTBE, DME or acetonitrile that contains 1.5-3 equivalents of NaH or t-BuONa or t-BuOK under nitrogen protection, stirring for 10-30 minutes to 1 hour at room temperature, adding dropwise 1.0 to 2.5 equivalents of iodides, bromides or chlorides with 10% NaI or KI, or activated alcohols, stirring the mixtures at room temperature for 30 minutes to 1 hour, monitoring the reaction by TLC, heating to 40-90° C., until the reaction is complete; quenching saturated NH$_4$Cl aqueous solution, adding ethyl acetate or dichloromethane or petroleum ether or toluene or MTBE or DME and fully mixing, separating organic phases, extracting aqueous phase three times, drying the combined organic phase with Na$_2$OS$_4$, filtering, removing the organic solvent in vacuum; obtaining solid product by recrystallization and oil or liquid product by purification through extraction or silica gel column chromatography;

adding 1 equivalent of alcoholic raw material to a solvent which is TI IF, acetone, ethyl acetate or acetonitrile, dichloromethane, chloroform, toluene, DME, MTBE, chlorobenzene or DMF that contains 1-3 equivalents of NaOH or KOH or Bu$_4$OH and 10-20% tetrabutylammonium bromide under nitrogen protection, stirring for 5-30 minutes at room temperature, adding dropwise 1.0-3.0 equivalents of iodides, bromides or chlorides with 5-30% NaI or KI, or activated alcohols, stirring the mixtures at room temperature for 1-3 hours, heating to 40-100° C. and reacting for 1-25 hours, monitoring the reaction by TLC until the reaction is complete, obtaining solid product by recrystallization, and oil or liquid product by purification through extraction;

or adding dropwise 1 equivalent of thiol to a solution which is dried THF, to DCM, acetone, THF, DME, acetonitrile or ethyl alcohol, methyl alcohol, chloroform, toluene or DMF that contains 1.0-3.5 equivalents of iodides, bromides or chlorides with 5-30% NaI or KI, or activated alcohols, then adding $Na_2CO_3$ or $K_2CO_3$, NaOH, KOH, $Bu_4OH$ or $NEt_3$ or DMAP or DBU or DIPEA or pyridine, stirring the mixtures at room temperature for 30 minutes, and then heating to 40-90° C. and stirring for 5-12 hours, monitoring the reaction by TLC until the reaction is complete; adding NaCl saturated aqueous solution and an equal amount of ethyl acetate or dichloromethane to the reaction system, fully mixing, separating organic phases, washing aqueous phase three times with the same organic solvent, drying the combined organic phases with $Na_2OS_4$, filtering, removing the organic solvent in vacuum; obtaining solid product by recrystallization, and obtaining liquid or oil product by extraction or silica gel column chromatography;

or dissolving 1 equivalent of amine in a solvent which is dichloromethane, ethyl acetate, acetone, acetonitrile, THF, ethanol, methanol, chloroform, MTBE, DME, toluene or DMF, stirring under nitrogen and adding dropwise 1-3 equivalents of organic iodides, organic bromides or organic chlorides, or activated alcohol compounds to the same organic solvent containing 1-3 equivalents of NaOH or KOH or $Bu_4OH$ or $K_2CO_3$ or $Na_2CO_3$ or DIPEA or $NEt_3$ or pyridine, adding 5-30% butyl tin bromide at the time of the addition of the inorganic base, reacting for 1-3 hours at room temperature, heating to 40 to 90° C. and stirring for additional 1-25 hours; cooling, washing alkaline and water-soluble impurities with the aqueous solution of $NH_4Cl$, obtaining solid product in organic phases by recrystallization, and oil or liquid product by purification through extraction or silica gel column chromatography;

or dissolving or suspending 1 equivalent of amine and equivalent of base in a solvent which is anhydrous dichloromethane, THF, MTBE, DME, acetone, cyano cyanide, chloroform, toluene or DMF, adding dropwise a solution of 1-2 equivalents of carboxyl chloride in the same dry solvent at 0-10° C. under nitrogen protection, stirring the mixture at 0-10° C. for 30 minutes to 2 hours at room temperature, monitoring the reaction by TLC until the reaction is complete; adding dichloromethane, ethyl acetate, toluene, DME or MTBE and 0.1N iced hydrochloric acid solution, mixing and then isolating organic phases, washing aqueous phase with the same organic solvent twice, drying the combined organic phases with anhydrous $Na_2SO_4$, filtering, concentrating; obtaining solid product in organic phase by recrystallization, and obtaining oil or liquid product by silica gel column chromatography or extraction;

or controlling the average molecular weight of the polymer products ranging from 1000 to 5000 daltons by adjusting the number of n;

dissolving 1 equivalent of diamine, polyamine in dry dichloromethane, ethyl acetate, THF, acetone, acetonitrile, ethanol, methanol, chloroform, toluene or DMF (1:5-15, w/v), and then stirring and adding dropwise polyiodinated, polybrominated or polychlorinated organic raw materials under nitrogen protection, stirring for 30 minutes at room temperature, and then heating to 40-100° C. and reacting for 6-72 hours, controlling the average molecular weight of the polymer product with reaction temperature and time, filtering to produce solid powder product, obtaining solid product by washing 3 times with dichloromethane to, or obtaining oil product sticky oil product by extraction.

5. The method for preparing multifunctional synergistic polymer anti-oxidation stabilizer as claimed in claim 4, comprising reaction scheme as following:

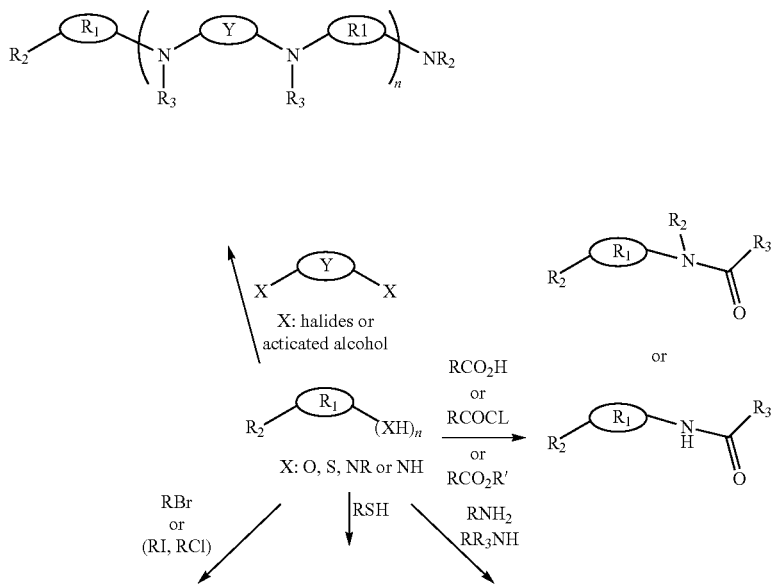

-continued

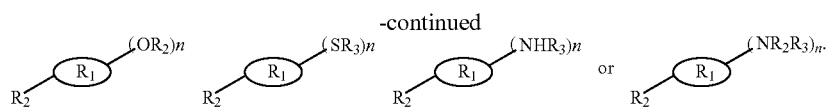

6. An application of the multifunctional synergistic polymer anti-oxidation stabilizer as claimed in claim 1 as an antioxidant.

7. The application of the multifunctional synergistic polymer anti-oxidation stabilizers as claimed in claim 6 in plastics, rubbers, petroleum, coatings, fiber products or paintings.

8. The application of the multifunctional synergistic polymer anti-oxidation stabilizer as claimed in claim 6, wherein —X—R in the multifunctional synergistic polymer anti-oxidation stabilizer is —(OR3)n, —(SR3)n, (NHR3)n or —(NR2R3)n, or wherein —X—R is

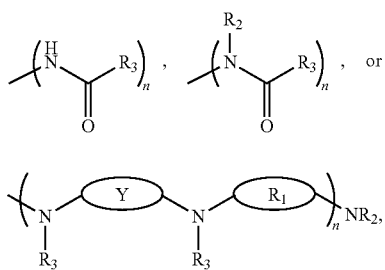

the formula turned into as the following formula:

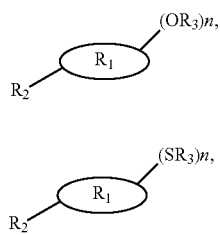

-continued

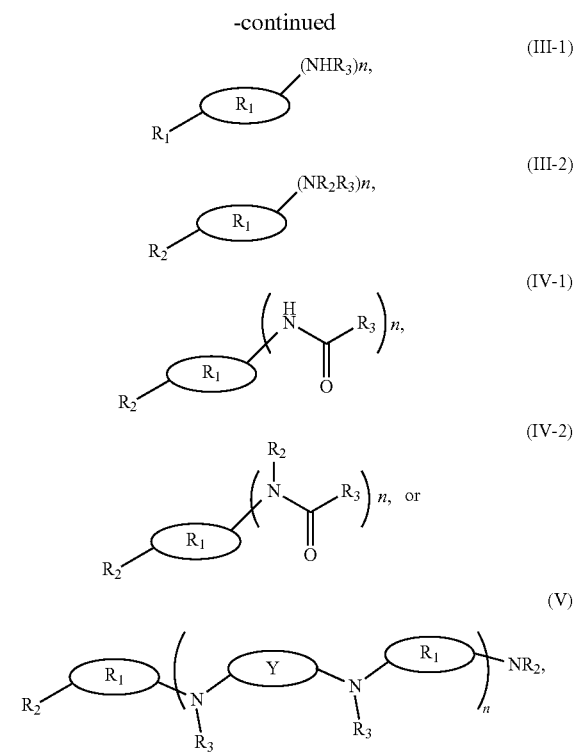

the R3 is H, an aliphatic side chain, an aromatic side chain, a mixed aromatic/aliphatic side chain, or a side chain having heteroatoms including S, O, N; n is a positive integer.

9. The application of the multifunctional synergistic polymer anti-oxidation stabilizer as claimed in claim 6, wherein example structures of the multifunctional synergistic polymer anti-oxidation stabilizer is:

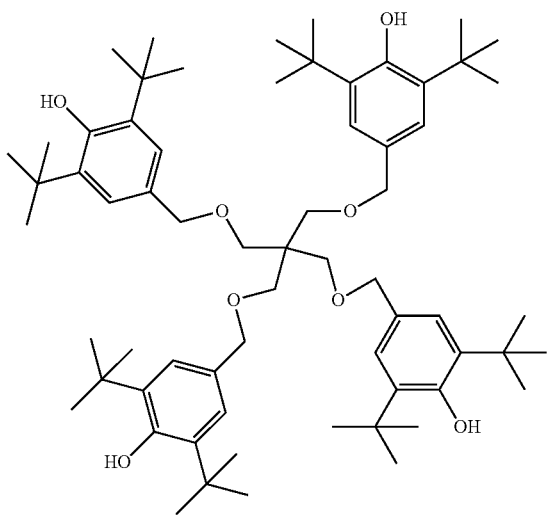

,

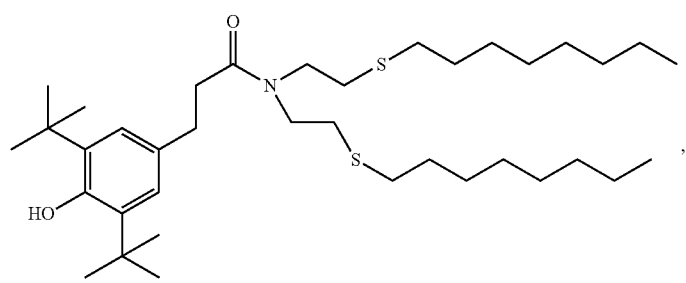
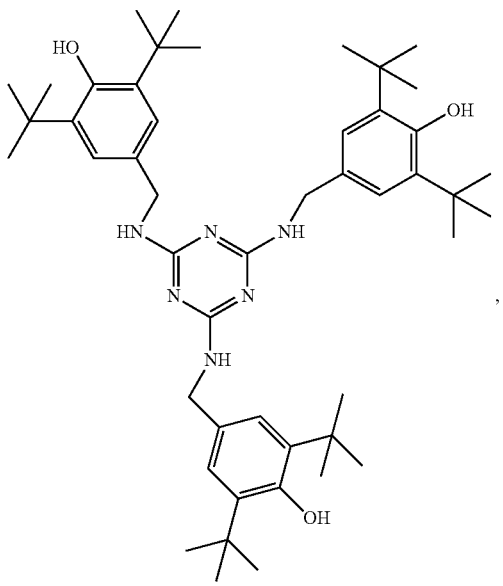
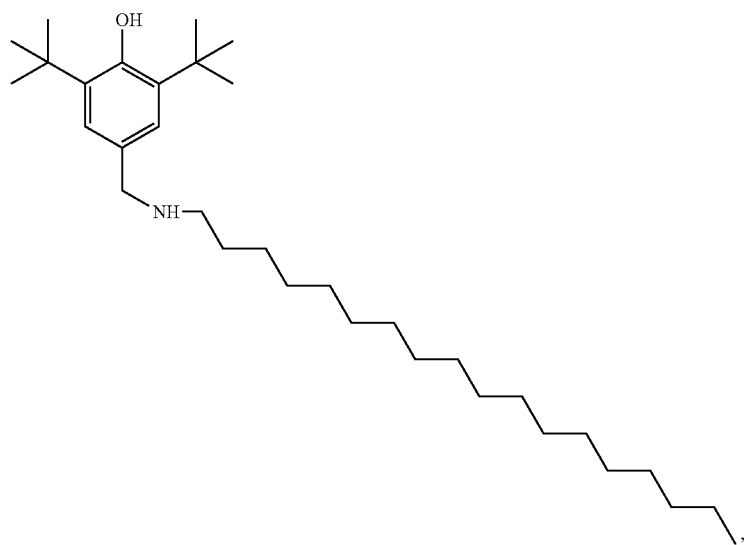
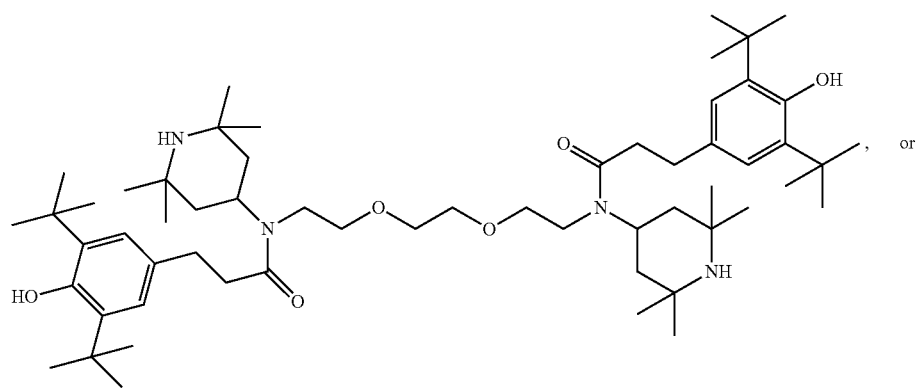

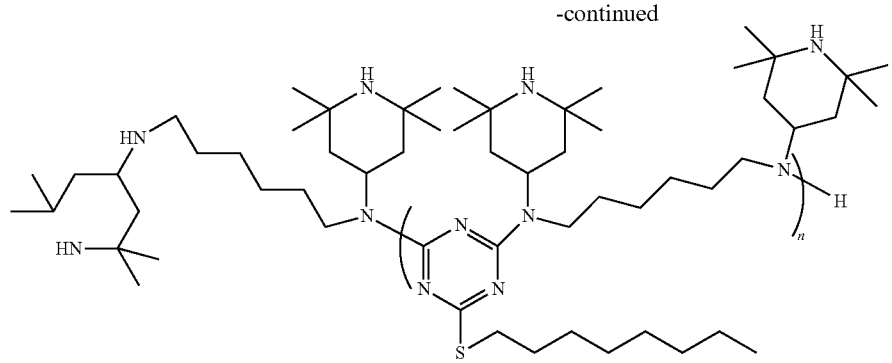
* * * * *